United States Patent
Pontecorvo

(10) Patent No.: US 11,766,383 B2
(45) Date of Patent: Sep. 26, 2023

(54) DISPOSABLE NASAL AND EYE WASH DISPENSER

(71) Applicant: Gary J. Pontecorvo, Stockton, NJ (US)

(72) Inventor: Gary J. Pontecorvo, Stockton, NJ (US)

( * ) Notice: Subject to any disclaimer, the term of this patent is extended or adjusted under 35 U.S.C. 154(b) by 1132 days.

(21) Appl. No.: 16/449,290

(22) Filed: Jun. 21, 2019

(65) Prior Publication Data
US 2019/0388607 A1 Dec. 26, 2019

Related U.S. Application Data

(60) Provisional application No. 62/689,394, filed on Jun. 25, 2018.

(51) Int. Cl.
| | |
|---|---|
| *A61H 35/02* | (2006.01) |
| *A61M 3/02* | (2006.01) |
| *A61H 35/04* | (2006.01) |
| *A61M 39/00* | (2006.01) |

(52) U.S. Cl.
CPC ........... *A61H 35/02* (2013.01); *A61M 3/0262* (2013.01); *A61M 3/0279* (2013.01); *A61H 35/04* (2013.01); *A61H 2201/0157* (2013.01); *A61H 2201/1253* (2013.01); *A61H 2201/1688* (2013.01); *A61M 3/0245* (2013.01); *A61M 2039/0027* (2013.01)

(58) Field of Classification Search
CPC ..... A61H 35/02; A61H 35/04; A61H 2201/0157; A61H 2201/1253; A61H 2201/1688; A61H 2201/0111; A61M 3/0262; A61M 3/0279; A61M 2039/0027; A61M 3/0245; A61M 2205/7545; A61M 3/005; A61M 2210/0612; A61M 2210/0618; B65D 81/3272; B65D 81/3261
See application file for complete search history.

(56) References Cited

U.S. PATENT DOCUMENTS

| | | | |
|---|---|---|---|
| 5,116,315 A | 5/1992 | Capozzi et al. | |
| 5,178,354 A * | 1/1993 | Engvall | B65D 83/303 24/3.12 |
| 5,605,255 A | 2/1997 | Reidel et al. | |
| 5,759,169 A | 6/1998 | Marx | |
| 6,461,325 B1 | 10/2002 | Delmotte et al. | |
| 9,114,204 B2 | 8/2015 | Jeppson | |
| 2011/0264122 A1 | 10/2011 | Bonino et al. | |
| 2013/0325059 A1 | 12/2013 | O'Neill | |
| 2017/0156981 A1 | 6/2017 | Ito | |
| 2018/0050163 A1 | 2/2018 | DeAnglis et al. | |
| 2019/0184088 A1 * | 6/2019 | Mechor | A61M 11/008 |

FOREIGN PATENT DOCUMENTS

| | | |
|---|---|---|
| KR | 101817973 B1 | 1/2018 |
| WO | 2017011361 A1 | 1/2017 |

OTHER PUBLICATIONS

Steven Park, May 20, 2015, doctorstevenpark.com, pp. 1, 3 (Year: 2015).*

* cited by examiner

*Primary Examiner* — Bhisma Mehta
*Assistant Examiner* — Phoebe Anne Staton
(74) *Attorney, Agent, or Firm* — Gearhart Law LLC; David Postolski

(57) ABSTRACT

An apparatus for rinsing sinuses or eyes, comprising a hand crushable container containing saline solution, and a dispenser configured to make a liquid tight seal with the container at one end, and a liquid tight seal with a nostril or an eye socket at the other end.

12 Claims, 6 Drawing Sheets

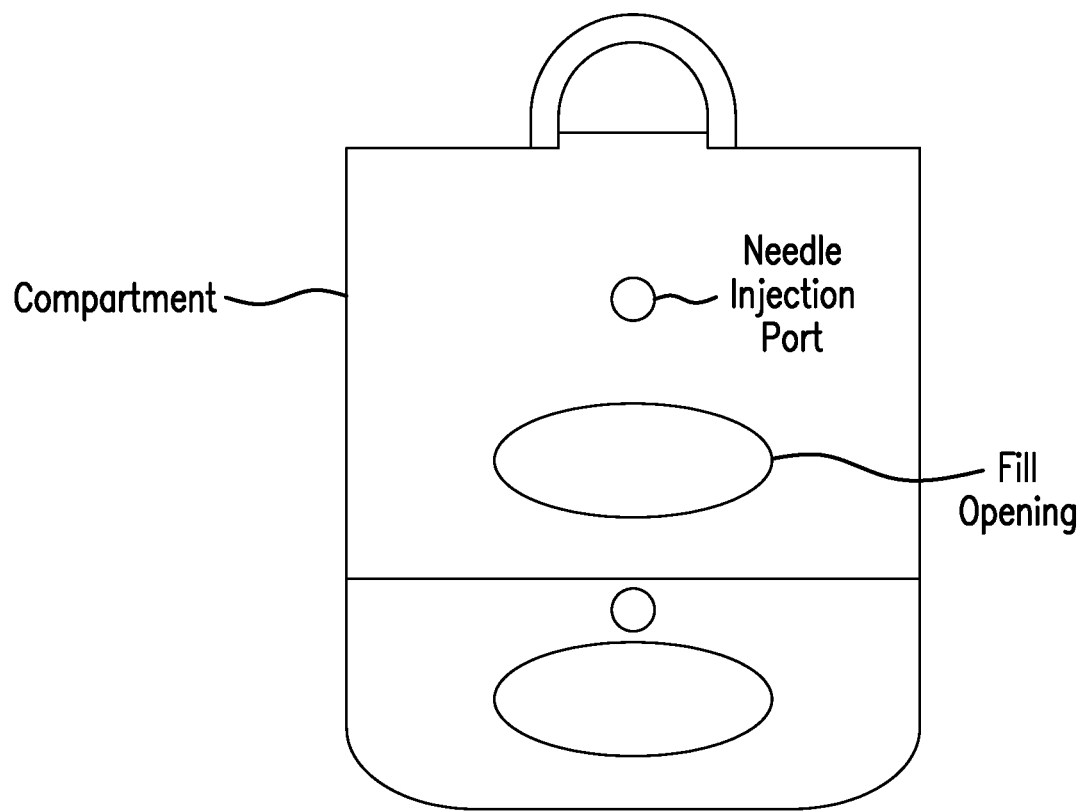
FIG.5C
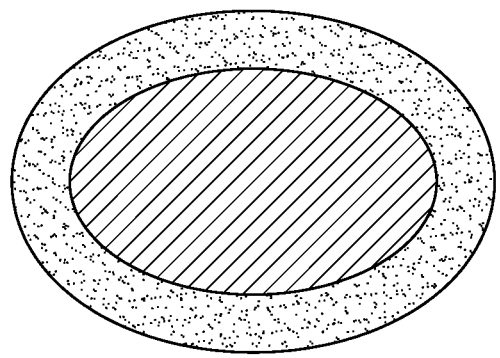
FIG.5D
FIG.5E

DISPOSABLE NASAL AND EYE WASH DISPENSER

PRIORITY CLAIM

This application is a United States utility application having priority to U.S. provisional application Ser. No. 62/689,394, filed Jun. 25, 2018 entitled Disposable Nasal and Eye Wash Dispenser, the entirety of which is hereby incorporated by reference as if fully set forth herein.

FIELD OF THE EMBODIMENTS

This invention relates to aqueous solution dispensers, and in particular to a disposable single-use nasal and eye wash dispenser.

BACKGROUND

Sinuses are hollow spaces within the bones of the face. People who experience chronic nasal discomfort, sinusitis, rhinitis, and the like may utilize a nasal rinse daily. An individual who has had sinus/nasal surgery must also irrigate their sinuses, multiple times a day. When at home, it is common to place a saline solute such as powdered sodium chloride mixed with a small amount of sodium bicarbonate, into a re-usable plastic bottle. The saline solute may be poured into the bottle from a premeasured single use packet. Distilled water is also poured into the bottle from a large (e.g., gallon-sized) container. The solute dissolves in the water to form an aqueous solution for flushing the sinuses, typically by pouring or pushing the solution into one nostril and letting it flow out of the other.

The sinus cavities are lined with a membrane called mucosa, which can become inflamed due to conditions such as sinusitis and rhinitis. Common symptoms include stuffy nose, nasal discharge, and headache. These can be caused by infections, disease, smoke, or other irritants. The same symptoms can be caused by allergies, which result from minute airborne particles called allergens that are breathed in and attach to the mucosa. Common allergens include mold, pet dander, and pollen. These and other particulates may also come into contact with the eyes, causing eye irritation.

Various methods to treat symptoms of sinus and eye irritation and disease are known. In particular, a saline solution wash can reduce the symptoms by rinsing and washing away mucus, allergy creating particles, and other irritants. Prior art means of doing so present challenges when away from home, and in particular when traveling. Containers of premixed saline solutions are available, but the containers can be expensive, heavy, inconvenient to carry and use, and may expire if not used for extended periods. Moreover, utilizing a pre-mixed saline solution does not allow for a specific amount or concentration of saline solution, which can be prescribed by a doctor, to be pushed into the nasal/eye cavity. Prior art apparatus is known for use with a premeasured amount of aqueous solution, which is poured into a reusable container from a single use vial. However, the containers must be cleaned after each use and stored for reuse. Furthermore, vials and other containers of solution larger than a few fluid ounces may also be flagged at a security check point prior to air travel. Saline solutions can alternatively be prepared by the user when traveling, but there may be concerns regarding cleanliness or contamination of the water or other ingredients, and ensuring proper concentration and pH of the solution. Thus, there is a need for improvements in preparing, using, and traveling with sterile, uncontaminated, properly concentrated and pH balanced saline solution and containers for flushing sinuses or eyes.

SUMMARY

The present invention is directed to dispensing a premeasured amount of saline solution to rinse sinuses or eyes. The apparatus comprises a container with a port with which a dispenser makes a liquid tight connection. The dispenser is configured to make a liquid tight seal with a nostril or eye socket. The container is hand crushable and can be squeezed to push the saline solution out through the dispenser to rinse a sinus or eye. Furthermore, pre-mixed saline solution can be stored in the container, and the solution stays combined until use. After use, at least a portion of the container may be recyclable.

The saline solution comprises distilled water, sodium chloride, and sodium bicarbonate. It may be premixed, or can be made by dissolving premeasured solute in a single use container of distilled water. In either case, the solution may be isotonic with tissues of the sinus or eye. The apparatus is convenient to carry, easy to assemble, and is disposable after use.

A method for washing an eye or nasal passage comprises removing a seal on a port of a container of saline solution, attaching a liquid dispenser to the port to form a liquid tight connection, pressing the dispenser against a body part or opening to form a liquid tight seal, and squeezing the container to push the saline solution out of the container and into the opening. The opening may be a nostril or an eye, although other openings may also be washed, such as an ear, or a wound. Moreover, the solution dispensed may include other or additional solutes, such as a topical antibiotic or anesthetic. The container may be configured with a barrier to keep solute and solvent separated until use. The solution must be made before it can be used by removing or breaching the barrier and mixing the solute and solvent together.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate disclosed embodiments and/or aspects and, together with the description, serve to explain the principles of the invention. The embodiments described are not intended to be limiting. Instead, the scope of the invention is determined by the claims.

In the drawings:

FIGS. 5C, 5D, and 5E illustrate enhancements to a fluid container with internal compartments in accordance with the disclosure.

DETAILED DESCRIPTION

Figure 1:
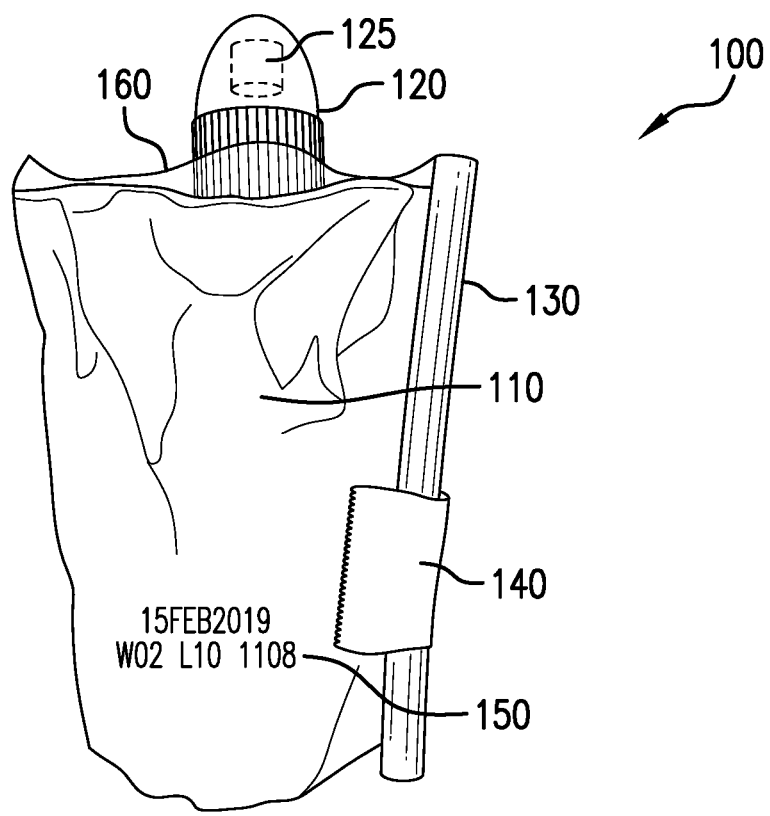
FIG. 1 is an exemplary embodiment in accordance with the disclosure.

Aspects of exemplary embodiments of the claimed invention will now be described with reference to the drawings, in which identical elements have the same reference numerals. These embodiments are provided by way of explanation of the present invention, which is not intended to be limited thereto. Those of ordinary skill in the art may appreciate upon reading the present specification and viewing the present drawings that various modifications and variations can be made thereto. In addition, it is noted the disclosure pertains to embodiments that may include a variety of solvents, solutes, and dispensers. Unless the context indicates otherwise, the term "distilled water" may be used herein to refer to any solvent; the term "sodium chloride" may be used to refer to any solute; and the term "aqueous solution" to refer to any solution comprising a solvent and a solute. It will be readily understood that the components of the present invention, as generally described and illustrated in the figures herein, may be arranged and designed in a wide variety of different configurations. Thus, the following detailed description of the embodiments and aspects of various apparatus and methods, and the illustrated embodiments and aspects as represented in the attached figures, are not intended to limit the scope of the invention as claimed, but are merely illustrative of selected exemplary embodiments.

Embodiments illustrate an apparatus that provides individuals a simple, convenient way to flush bodily openings such as nasal cavities, eyes, open wounds, and the like. The apparatus is a hand crushable, disposable, single use container pre-loaded with a measured amount of aqueous saline solution or other appropriate fluid. In embodiments, after use at least a portion of the container may be recyclable. In embodiments, a measured amount of distilled water and a mixture of measured amounts of sodium chloride and sodium bicarbonate are separated from each other by a barrier within the container. The container is coupled to a fluid dispenser having a configuration appropriate for a specific use, for example, configured to make an effectively fluid-tight seal with a nostril, eye socket, or punctured body part. The solution exits the container through the dispenser when the container is squeezed in the hand. In embodiments, the container and/or dispenser is covered by a removeable seal or cap at the time of manufacture to maintain hygiene, safety and tamper control. In embodiments, the dispenser is removably attached to an outside surface of the container, for example with an adhesive. The dispenser is detached from the container, and coupled with a port of the container to make a fluid-tight seal. The container may have a flat bottom, and the port may protrude from the top of the container.

In an embodiment, prior to use the container is filled with premixed saline solution.

In other embodiments, distilled water and a powdered mixture containing sodium chloride and sodium bicarbonate are stored in separate chambers, and the powdered mixture must be added to and dissolved in the distilled water in the container to form the saline solution.

In embodiments, the chambers may be formed inside the container separated by a breachable impermeable barrier. In an embodiment, the barrier comprises a flexible material such as a plastic membrane or layer affixed to an inside circumference of the container to form a fluid tight seal. In an embodiment, the material has a tab that can be pulled from the outside of the container to breach the barrier by peeling, tearing, or sliding the material to mix the powder and the water. In another embodiment, the material has a portion configured to be breachable without fragmenting by manipulating the exterior of the container, to mix the powder and the water. After mixing, the container can be shaken and lightly manipulated to assure the powder is thoroughly mixed with and dissolved in the water.

In embodiments, the dispenser is packaged separately from the container, and a dispenser may be selected that is configured appropriately for a particular intended use. In embodiments, the dispenser may be attached to or otherwise packaged together with the container. In embodiments, the container port may be covered with a removable cap. The cap may be secured to the container in any manner known in the art, for example by a threaded or ribbed connection so the cap can be screwed or pulled off the port. In embodiments, the dispenser port may additionally or alternatively be sealed with a removable seal. For example, in an embodiment the dispenser may be screwed or pulled off a threaded or ridged end of the container port, and a seal at the top of the container port end is removed and discarded. The dispenser can then be screwed or pushed back onto the threads or ridges to form a liquid tight seal. In embodiments, the dispenser itself may comprise a tube element separable from a dispenser head element. The tube and the dispenser head may separately be attached to or otherwise packaged with the container, and may also be screwed or pushed together into matching threads or ridges to make a liquid tight seal.

In use, the dispenser is pressed against a bodily opening to form a substantially liquid tight seal. The container is then squeezed in the hand to push the saline solution out though the dispenser to flush the opening. After use, the container and dispenser can be discarded. In embodiments, the container and/or the dispenser may be made of a recyclable or biodegradable material such as polyethylene terephthalate (PET) or other plastic.

Advantageously, the disclosed apparatus separates the solvent (such as water) and solute (such as sodium chloride) within the same package. The package is portable and travel ready, and can be sized and configured based on intended use and/or travel restrictions. The entire package is disposable, and some or all of it may be recyclable. Moreover, the same container and/or dispenser configurations can be utilized for other portable medical solutions.

Referring now to FIG. 1, an exemplary embodiment 100 is shown prior to assembly and use of the apparatus. As shown, container 110 is made of a packaging material that can easily be crushed in the user's hand to push the contents out. In FIG. 1, the packaging material contains at least a plastic layer and an opaque foil layer, although other materials can be used, such as colored or transparent materials. In an embodiment suitable for use during air travel, the container may be sized to contain amount of liquid permitted by the Transportation Security Administration (TSA) without special accommodation, currently 3.4 fluid ounces (fl. oz.). Various embodiments include containers sized to hold different volumes. For example, a small packet holding half an ounce of saline solution (about 15 ml) may be sufficient to rinse a dirty contact lens, whereas a container for flushing a wound may hold a quart (about a liter) or more. It is contemplated a container for thoroughly flushing sinuses or for rinsing eyes may hold 8 fl. oz. (about ¼ liter). This is the size illustrated in FIG. 1.

As shown, the illustrated embodiment includes a plastic cap 120 that covers a container port (not shown in FIG. 1). Plastic cap 120 may also cover a small packet or cup of solute 125, that can be emptied through the port into the container 110 and dissolved therein. In an alternative embodiment, solute can be stored inside neck of the container, with a barrier separating the solute and the solvent that must be breached, and a seal at the top of the neck that must be removed. As shown, tube 130 is removably attached to side of the container 110, for example, with glue or tape. In an embodiment, the bottom of the container 110 is substantially flat to form a stable base on which the container can stand upright.

In embodiments, the interior of container 110 is unobstructed and filled with saline solution, or some other solution for use in other treatments, for example.

In other embodiments, the interior of container 110 includes a breachable barrier (not shown) separating the interior into two compartments. One compartment contains a liquid solvent such as distilled water, although other solvents may be used, for example, for other treatments. The other compartment contains a solute, such as a powdered mixture of sodium chloride and sodium carbonate, although other solutes may be used, for example, for other treatments. As shown in FIG. 1, an external tab 140 of the compartment-separating breachable barrier is shown extending through the material of container 110 and secured to the side of the container. The tube 130 is shown affixed to side of container and underneath tabs. In embodiments, the container or other packaging element may be marked, 150, with a date, serial or batch number, or the like. In embodiments, some or all of these packaging elements can be bound together in a plastic cover 160.

In embodiments, the container can have more than two compartments separated by more than one breachable barrier, for example for use in an application requiring keeping more than two ingredients separated prior to use. This may be used, for example, for a first application using a first solution, followed by a second application using a second solution with one or more additional ingredients, or for mixing or dissolving a plurality of compartmentalized ingredients in a specific order to make intermediate mixtures or solutions.

To use the embodiment illustrated in FIG. 1, the plastic cover 160 is removed. The compartment separator tab 140 is separated from the container 110, and the tube 130 is separated from the container 110. The tab 140 is then pulled in a direction substantially normal to the surface of the container 110 to breach the barrier therein, such as by peeling, tearing, or sliding the barrier, which is affixed to an internal circumference of the container 110 to form a liquid tight seal. When the barrier is breached, the contents of the compartments can be mixed together and dissolved inside the container 110. To ensure proper mixing, the sides of the container 110 can be squeezed, manipulated, shaken, and the like. The cap 120 is removed. A seal (not shown) covering the top of the container port is removed. In the illustrated embodiment, the cap 120 may be configured to be a dispenser head. The cap is manufactured to have a shape suitable for the intended use, with at least one hole for the solution to pass through during use. The tube 130 is attached to the bottom of the dispenser head 120, such as by pressing or screwing an end of the tube onto a matching connector of the dispenser head. The other end of the tube must be attached to the port of the container 110. The apparatus is then ready to be used. After the use is finished, the entire package may be discarded. Some or all of the apparatus may preferably be made of a recyclable material, and can be recycled.

In embodiments, the components making up the saline solution may be preselected and premeasured to make a solution that is either hypotonic, isotonic, or hypertonic with sinus or eye tissue, blood, or other natural fluid of the area to be flushed. It is well known that the water content of any bodily fluid moves through cell membranes it contacts. If the total concentration of all dissolved solutes in fluids on both sides of the cell membranes is not equal, there will be a net movement of water molecules into or out of the cell. Whether the movement is into or out of the cells of the tissues being flushed depends on whether the rinsing fluid is isotonic, hypotonic, or hypertonic with the tissues. When the aqueous solution is isotonic with the tissue being flushed, the total concentration of dissolved solutes is the same on both sides of cell walls in the tissue, so there is no net movement of water through the cell walls. Hyper- or hypo-tonic solutions may damage cell walls. Accordingly, it is generally desirable for a saline or other aqueous solution to be isotonic with the tissues it comes into contact with. One such solution is called Ringer's solution, which is a solution of several salts dissolved in water. Typically the salt(s) include at least one of sodium chloride, potassium chloride, and calcium chloride, with sodium bicarbonate added to balance the pH of the solution. Other or additional additives can include cellular chemical fuel sources such as dextrose, antibiotics, antifungals, anesthetics, and the like. Another such solution is called Ringer's lactate solution (RL), which is a mixture of sodium chloride, sodium lactate, potassium chloride, and calcium chloride in water. Other solutions with similar molar concentrations may alternatively be used.

Figure 2A:
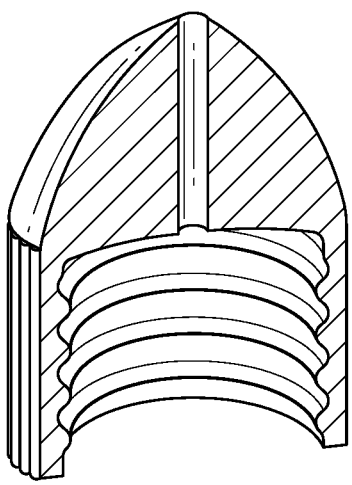
FIGS. 2A and 2B are exemplary dispenser heads embodiments for washing sinuses in accordance with the disclosure.
Figure 2B:
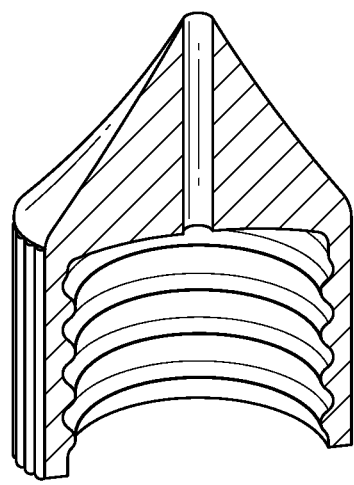

Various configurations of the components of the claimed apparatus may be used. For example, the tube can be made in one piece with the dispenser head as a complete dispenser component. Or as described previously, the tube may be removably coupled to the dispenser head to make a complete dispenser component. Moreover, different dispenser head configurations may be used for different applications such as a nasal rinse or an eye wash, or to accommodate users of different sizes such as a child or an adult. When fluid is to be dispensed into an orifice such as a nostril, it is advantageous for the dispenser to having an exit port size and surface configuration suitable to make a liquid tight seal with the orifice. FIGS. 2A and 2B illustrate two exemplary dispenser head configurations that may be used for flushing a user's sinus cavity, although other configurations may alternatively be used. In currently preferred embodiments, the apparatus components are packed in a single package that can be conveniently tossed into a suitcase or travel bag, or stored at work or another location away from home. When ready to use, the components are unpackaged and assembled.

In an embodiment having distinct and separable fluid container, flexible tube, and dispenser head components, a first end surface of the tube is configured to match a surface of the container port. This matching pair of surfaces can be pushed or screwed together make a liquid tight seal. Likewise, the dispenser head can be configured to match the other end of the tube, to be pressed or screwed onto that end to make another fluid tight seal.

The matching surface pairs (i.e., an end of the tube coupled to the container port, and the other end of the tube coupled to a connector on the dispenser head) are configured with matching surfaces to make their respective water tight seals. There is a variety of matching surfaces that can be used to couple the components together, including ribbed, threaded, and smooth surfaces with a latching element to prevent the surfaces from decoupling. Either of the coupling components may be configured as a male end, to be inserted into a matching female end of the other component being joined.

Figure 3A:
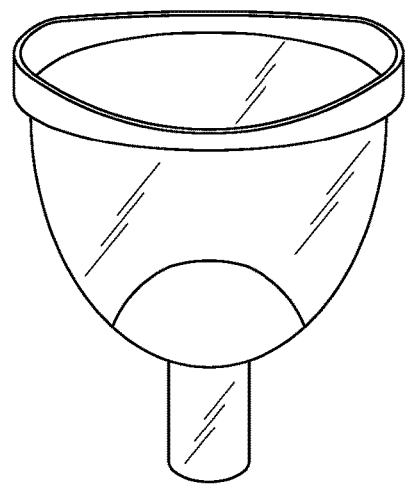
FIGS. 3A and 3B are exemplary dispenser head embodiments for flushing an eye and a wound, respectively, in accordance with the disclosure.
Figure 3B:
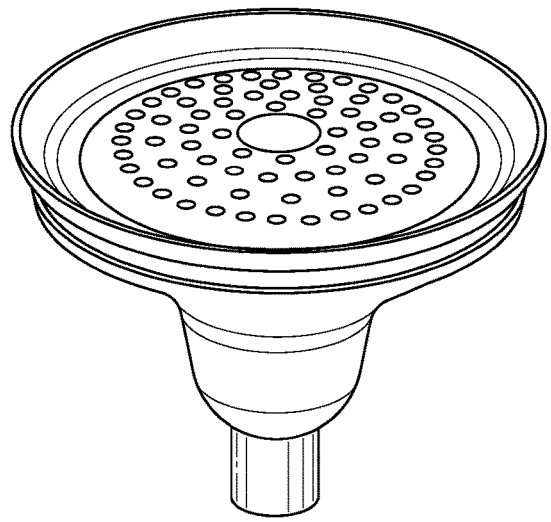

FIG. 3A illustrates a dispenser head suitable for use as an eye cup to rinse a user's eye. The eye cup can be pushed or screwed onto an end of the tube as described above, with the other end of the tube coupled to the container port. FIG. 3B illustrates a dispenser head configured as a shower head-like structure suitable for flushing an open wound. The periphery of this dispenser head can be pressed against the tissue around the wound to form a liquid tight seal. Advantageously, this allows the wound to be flushed several times in a row using the same apparatus, thereby promoting a more thorough flushing than a single rinse may achieve.

Figure 3C:
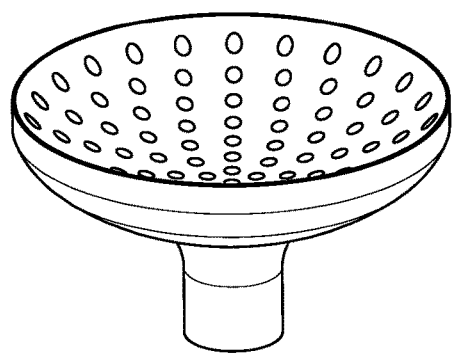
FIGS. 3C and 3D illustrate the ability of an exemplary dispenser head to focus a spray, in accordance with the disclosure.
Figure 3D:
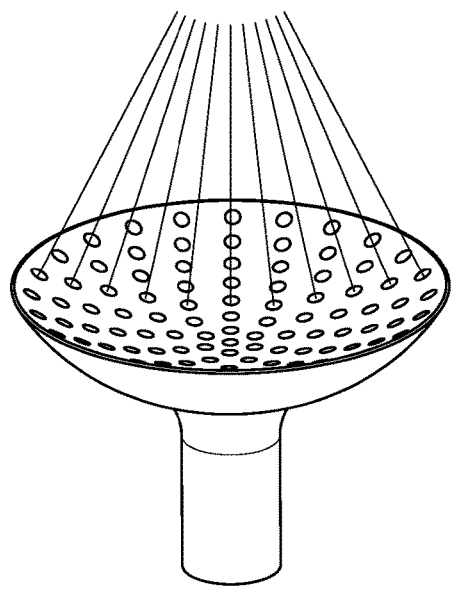

In embodiments, the dispenser head may be configured to have a plurality of holes to create a spray. In embodiments, the holes can be configured to concentrate the spray. FIGS. 3C and 3D illustrate such an embodiment before and during use, respectively.

Figure 4A:
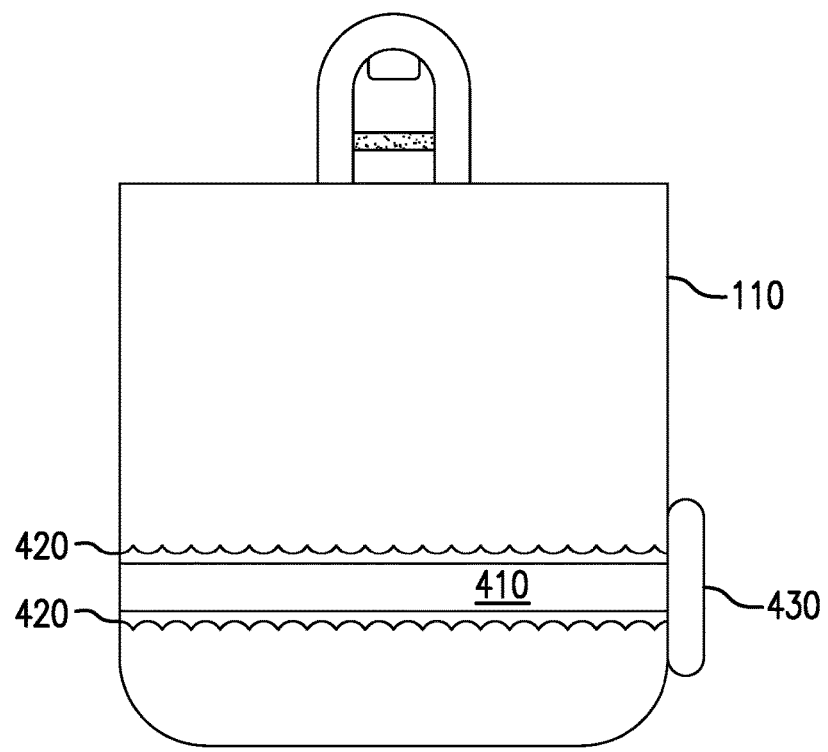
FIGS. 4A and 4B illustrate a first exemplary embodiment of a fluid container with internal compartments in accordance with the disclosure.
Figure 4B:
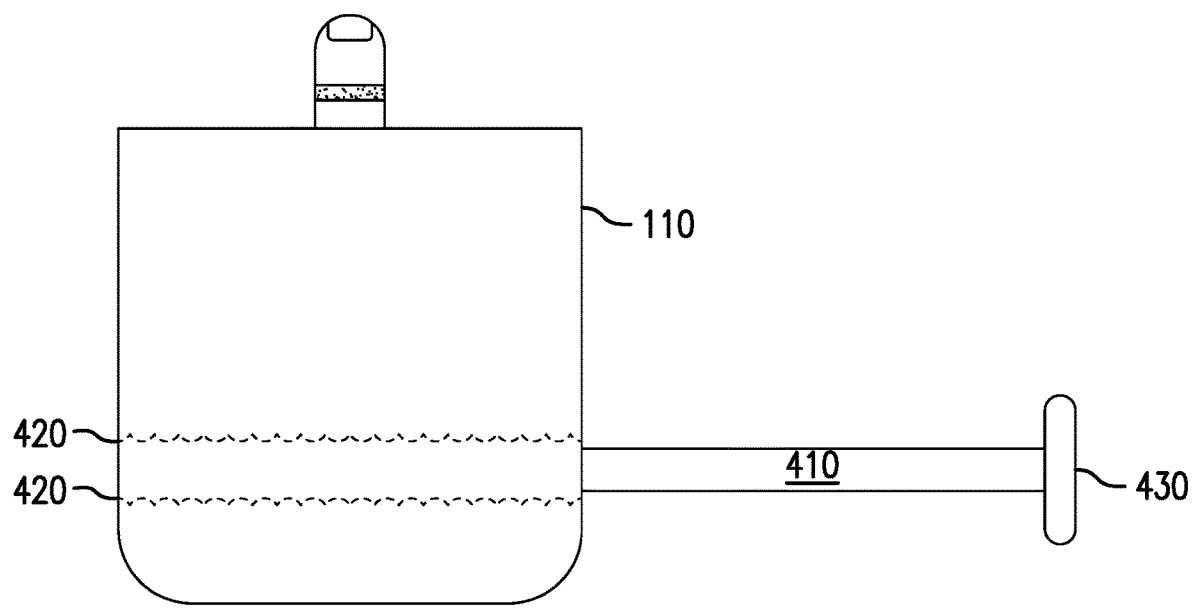

In embodiments, a barrier can be disposed inside the container to separate the distilled water or other solvent from a mixture of sodium chloride and sodium bicarbonate or other solute, until the apparatus is to be used. For use, the barrier is breached and the sodium chloride and the sodium bicarbonate are dissolved in the distilled water to form the saline solution. As shown in FIG. 4A, in an embodiment the barrier 410 is slidably coupled to adjacent inside surfaces of the container, for example, using collinear rails 420 permanently coupled to adjacent interior surfaces of the container 110. In embodiments, the barrier is breached by pulling a tab 430 contiguous with the barrier 410 and extending out of the container through a liquid-tight slot, to decouple at least a portion of the barrier 410 from the inside surface of the container. FIG. 4B shows the barrier 410 pulled all the way out of the container 110, leaving rails 420 empty (signified by dotted lines).

Figure 5A:
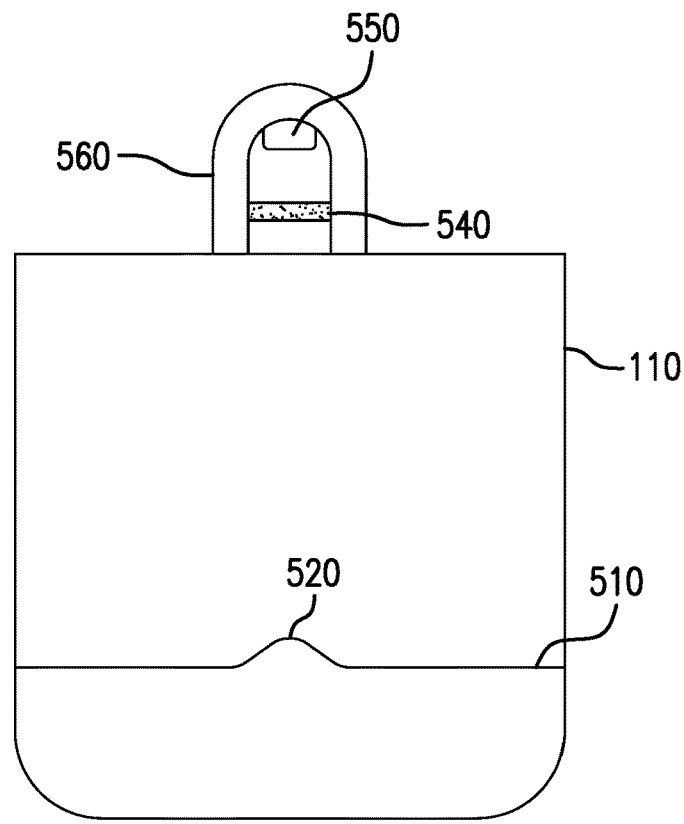
FIGS. 5A and 5B illustrate a second exemplary embodiment of a fluid container with internal compartments in accordance with the disclosure.
Figure 5B:
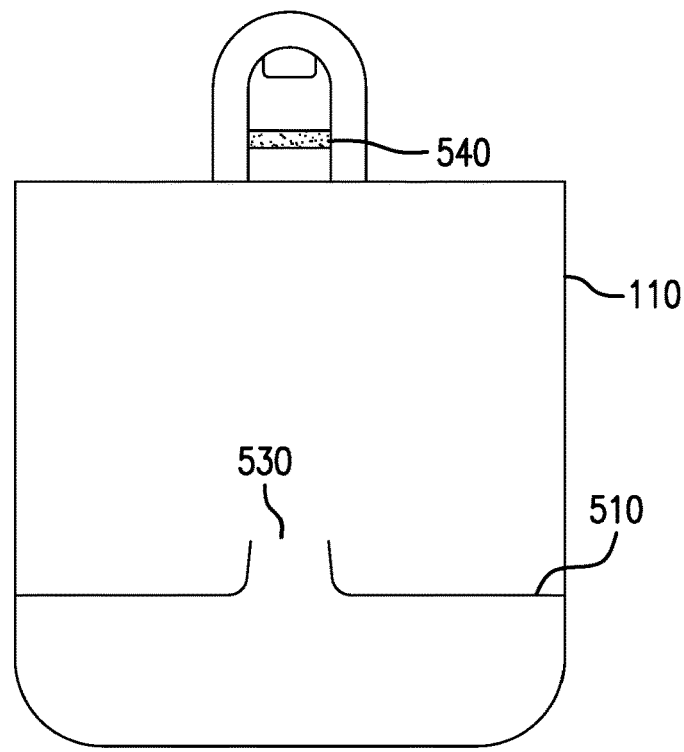

In another embodiment illustrated in FIG. 5A, the barrier 510 inside the container 110 may be permanently coupled directly to a circumferential inside surface of the container. In this embodiment, the barrier comprises at least one preferentially tearable or breakable portion 520, that can be breached without fragmenting the barrier. The barrier is breached by manipulating an outer surface of the container 110, such as by squeezing one compartment to increase its internal pressure, or by rubbing the sides of the container together to rupture the barrier, or the like. In embodiments, the preferentially tearable or breakable portion is configured as the thinnest part of the barrier, to tear or break 530 without dislodging any of the barrier that can be carried by the solution out of the container, as shown in FIG. 5B. In an embodiment, the container port may be configured to have a screen or filter 540 through which the fluid must flow when exiting the container, to catch any barrier fragments that may inadvertently have been made as the barrier was breached.

In embodiments, the apparatus packaging includes a removable seal 550 covering the container port, to prevent any contamination of the fluid inside, and to provide a visual cue if pierced to indicate the package may have been tampered with. In embodiments, the packaging may additionally or alternatively include a removable protective cap 560 covering the container port. In such embodiments, the apparatus packaging may further comprise a compartment (not shown) under the protective cap containing the mixture of sodium chloride and sodium bicarbonate or other solute, to keep it separate from the distilled water or other solvent in the container. The mixture is then introduced into the container through the container port to be dissolved in the fluid in the container.

Use cases for the foregoing include mixing juices or beverages at the time of use, for example to obtain different flavors. Embodiments may be used for mixing protein or health drinks at the time of use, such as milk and/or water, and whey or soy protein. Embodiments may also be used for mixing compounds to form a gel at the time of use, or for mixing prescription medication at the time of use. In particular, for prescriptions which need to be kept separate from solution and only mixed at the time of use, such as a nasal solution with budesonide stored in the sealed compartment and emptied into distilled water at the time of use.

Embodiments, such as those illustrated in FIGS. 4A and 5A, may be modified by adding the enhancements shown in FIG. 5C. As shown, modifications can be made to the top compartment, or the bottom compartment, or both. In one aspect, a fill opening can be included in one or both compartments, spaced apart from the barrier between compartments. The fill opening can include an opening in a wall of a compartment with an edge shaped to match an edge of a removable sealing cover. The sealing cover can be removed and one or more substances can be placed through the uncovered hole into the compartment. The cover may then be replaced making a tight seal, and the compartments used as previously disclosed.

In an exemplary operation, the fill opening may be kept closed at the time of manufacturing to keep the compartments sealed. When the cover is installed sealing and covering the fill opening, the integrity of the compartment and the overall container to hold its contents is the same as if the fill opening was not part of the container. Thus, the fill opening has a removeable and replaceable sealing cover. In an embodiment, the sealing elements may have rails imbedded in the side walls of the container in which a tongue on the edge of the sealing cover fits to create the seal. The sealing cover can have the rails or lip in which each rail fits on each side of the counter wall.

The fill opening can be utilized to insert substances into its compartment, such as saline crystals and powder medications and liquids or compound solutions, such as prescription solutions. The sealing cover may be removed to add these substances and replaced to close the fill opening. The container can then be utilized as described previously. The sealing cover may be attached to the container via a lanyard or the like to keep it close to the container.

In another aspect, a needle injection port can be including in one or both compartments. FIGS. 5D and 5E are perspective and side views, respectively, of an exemplary embodiment of a needle injection port, which can be used similarly to an injection point of an IV bag. An injection port may be used to add solutions such as medications to its compartment. A needle can be pushed through the Injection Port until its end is inside the compartment where the contents of the needle can be delivered into the compartment. The needle may then be removed and, similarly to an IV bag, the injection port will maintain the integrity of the compartment and container for use as previously described. Examples of compounded medications that may be suitable for use with an injection port include Clotrimazole in DMSO solution, Cyclobenzaprine/Ketoprofen transdermal gel, Dexamethasone iontophoresis solution, Fluconazole/Ibuprofen topical gel, Ketamine/Gabapentin transdermal gel, Ketoprofen 10% transdermal gel, LAT topical gel, Lidocaine/Hydrocortisone "rectal rocket" suppository, and the like.

The preceding embodiment provides the ability to add prescription(s), compound(s), solution(s) and the like to the container after it has been manufactured. The container may be manufactured with prescription(s), compound(s), solution(s) and the like inside separate compartments. Or, the compartments can manufactured empty, and prescription(s), compound(s), solution(s) and the like may be added to compartments of the container by a compound pharmacy or user, for example. Compound pharmacies that could utilize the new embodiments include, http://drugcrafters.com/prescribers/sports-medicine/examples-of-compounded-medications; https://www.verywellhealth.com/what-is-drug-compounding-2663861; http: https://www.reviewofophthalmology.com/article/compounded-drugs; //healthwayrx.com/pain-management; and others.

In an exemplary use case utilizing the disclosed container for eye wash purposes using compound solutions, one of the most common compounded drug used in ophthalmology is bevacizumab (Avastin). Although bevacizumab is FDA-approved to treat colorectal cancer, it is also commonly used "off-label" for use in ophthalmology. That is, it has not been through the rigorous FDA process required for approval to treat ophthalmic pathology. In general, compounded drugs are not FDA-approved, which means that their safety or effectiveness hasn't been verified. Nevertheless, ophthalmologists and other practitioners may use bevacizumab or other compounded drugs, for example to treat ophthalmic conditions such as including choroidal neovascularization, age-related macular degeneration, diabetic retinopathy and retinal vein occlusion. However, because the drug's manufacturer Genentech doesn't produce bevacizumab in doses suitable for intravitreal injections, single-use vials of the appropriate dose may be obtained from compounding pharmacies.

Figure 6:
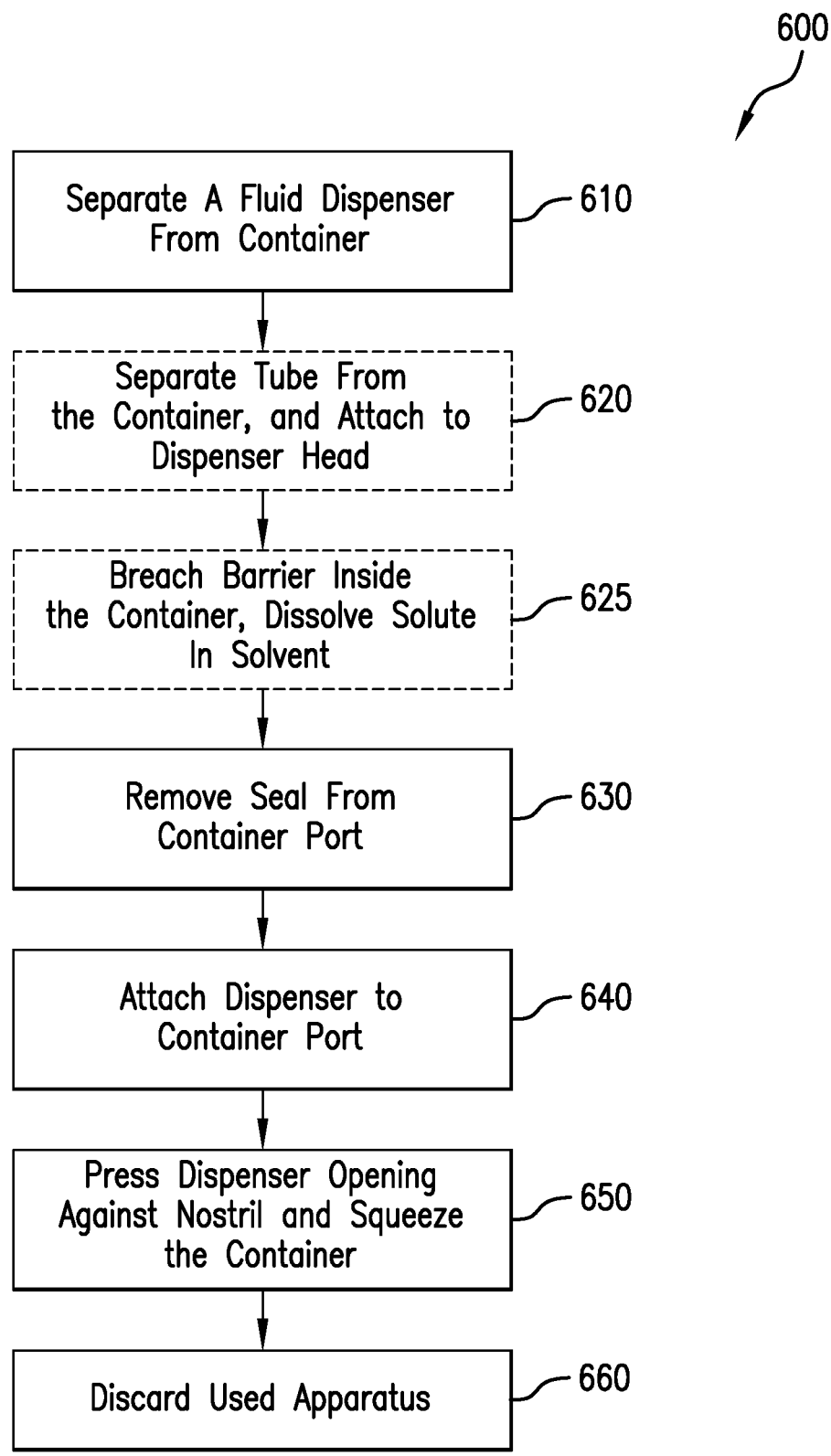
FIG. 6 is a flow diagram showing an exemplary method of using a fluid container to wash a user's sinuses in accordance with the disclosure.

FIG. 6 is a flow diagram illustrating an exemplary method 600 for rinsing a user's sinus cavity. Unless indicated otherwise, the following steps may be completed in any convenient order. The method includes separating 610 a fluid dispenser from a hand crushable container of saline solution to which it is attached. If the apparatus has separate tube and dispenser head components, the method includes removing the flexible tube from the container of saline solution to which it is attached, and assembling the dispenser component by attaching the tube to the dispenser head 620, making a liquid tight seal. If the container includes an internal barrier separating the solvent from the solute, the method includes breaching the barrier and combining 625 a mixture of sodium chloride and sodium bicarbonate from a first compartment as the solute, with distilled water in a second compartment as the solvent, to make the saline solution. A seal from a port of the container is also removed 630. The dispenser is attached 640 to the container port, making a liquid tight seal. An exit port of the dispenser of the assembled apparatus is then pressed to the user's nostril, and the user then squeezes the container with their hand 650 to push the saline solution out of the container, through the dispenser, into the sinus cavity, and out through the other nostril. After use, the entire apparatus can be discarded 660, completing the method.

In the foregoing, when introducing disclosed embodiment(s) or aspects thereof, the articles "a," "an," and "the" are intended to mean that there are one or more of the elements or aspects. Similarly, the adjective "another," when used to introduce an element, is intended to mean one or more elements. The terms "including" and "having" are intended to be inclusive such that there may be additional elements other than the listed elements.

Although the embodiments have been described with a certain degree of particularity, it is to be understood that the foregoing disclosure has been made only by way of illustration and not limitation. Numerous changes in the details of construction and arrangement of parts may be made without departing from the spirit and the scope of the invention as defined by the appended claims.

What is claimed is:

1. An apparatus configured for rinsing sinuses or eyes, the apparatus comprising:
   a hand crushable container containing saline solution, the container having a port through which the saline solution flows when the container is squeezed;
   the saline solution, comprising distilled water, sodium chloride, and sodium bicarbonate, configured for rinsing a sinus or an eye;
   a dispenser configured to make a first liquid tight seal with a nostril or an eye socket, and configured with the port of the container to make a second liquid tight seal; and
   a barrier, the barrier is located inside the container, wherein prior to a breach of the barrier, said barrier separates the distilled water from a mixture of the sodium chloride and the sodium bicarbonate, and wherein when the barrier is breached the sodium chloride and the sodium bicarbonate dissolve in the distilled water to form the saline solution.

2. The apparatus of claim 1, wherein the saline solution is isotonic with sinus or eye tissue.

3. The apparatus of claim 1, wherein the dispenser comprises:
   a flexible tube coupled to a dispenser head, the dispenser head having an exit port surface perimeter configured to make the first liquid tight seal with the nostril or eye, and a first end surface of the tube configured to connect with the container port to make a third liquid tight seal; and
   a second end surface of the tube configured to match an entry port surface of the dispenser head to make a fourth liquid tight seal.

4. The apparatus of claim 3, wherein the tube is removably attached to a side surface of the container prior to use, and is detached from the side surface and assembled with the container and the dispenser head.

5. The apparatus of claim 1, wherein the barrier is removably coupled to a circumferential inside surface of the container, and the barrier is breached by pulling a tab extending out of the container to decouple at least a portion of the barrier from the inside surface of the container.

6. The apparatus of claim 1, wherein the barrier is permanently coupled to a circumferential inside surface of the container, and the barrier comprises at least one preferentially tearable or breakable portion, and the barrier is breached by manipulating an outer surface of the container.

7. The apparatus of claim 6, wherein the at least one preferentially tearable or breakable portion is configured as the thinnest part of the barrier to tear or break without dislodging any of the barrier that can be carried by the solution out of the container.

8. The apparatus of claim 1, further comprising a removable seal covering the container port.

9. The apparatus of claim 1, further comprising at least one of an antibiotic and an anesthetic dissolved in the saline solution.

10. The apparatus of claim 1, wherein the container and dispenser are made of disposable materials.

11. The apparatus of claim 1, wherein the container has a flat bottom surface and can stand upright on a substantially level plane.

12. An apparatus for rinsing sinuses or eyes, the apparatus comprising:
- a hand crushable container containing saline solution, the container having a port through which the saline solution flows when the container is squeezed;
- the saline solution, comprising distilled water, sodium chloride, and sodium bicarbonate, for rinsing a sinus or an eye;
- a dispenser configured to make a first liquid tight seal with a nostril or an eye socket, and configured to connect with the port of the container to make a second liquid tight seal;
- a removable protective cap; and
- a compartment under the protective cap, wherein prior to the container containing the saline solution, said compartment contains a mixture of the sodium chloride and the sodium bicarbonate separate from the distilled water in the container, wherein when the mixture is introduced into the container through the container port, the sodium chloride and the sodium bicarbonate are dissolved in the distilled water to form the saline solution.

\* \* \* \* \*